(12) United States Patent
Hampp

(10) Patent No.: US 7,534,586 B2
(45) Date of Patent: May 19, 2009

(54) METHOD FOR PRODUCING BIOMASS

(75) Inventor: Norbert Hampp, Amöneburg-Roβdorf (DE)

(73) Assignee: K+S Aktiengesellschaft, Kassel (DE)

( * ) Notice: Subject to any disclaimer, the term of this patent is extended or adjusted under 35 U.S.C. 154(b) by 41 days.

(21) Appl. No.: 10/450,461

(22) PCT Filed: Dec. 12, 2001

(86) PCT No.: PCT/EP01/14600

§ 371 (c)(1),
(2), (4) Date: Jun. 13, 2003

(87) PCT Pub. No.: WO02/48381

PCT Pub. Date: Jun. 20, 2002

(65) Prior Publication Data

US 2004/0029233 A1    Feb. 12, 2004

(30) Foreign Application Priority Data

Dec. 13, 2000    (DE) ............................... 100 62 030

(51) Int. Cl.
*C12P 21/00* (2006.01)
*C12P 1/04* (2006.01)

(52) U.S. Cl. .................. 435/71.2; 435/71.1; 435/170
(58) Field of Classification Search .............. 435/252.1, 435/243, 822
See application file for complete search history.

(56) References Cited

U.S. PATENT DOCUMENTS 4,826,769 A     5/1989   Menger
5,922,843 A  *  7/1999   Tan et al. .................... 530/350

FOREIGN PATENT DOCUMENTS

DE         269 163 A     6/1989

OTHER PUBLICATIONS

Bergey's Manual of Determinative Bacteriology. 1994, pp. 742-743.*
Rodriguez-Valera, F., "Biotechological potential of halobacteria," Biochem. Soc. Symp., vol. 58, p. 135-147, 1992.

* cited by examiner

*Primary Examiner*—Vera Afremova
(74) *Attorney, Agent, or Firm*—Sutherland Asbill & Brennan LLP

(57) ABSTRACT

The invention relates to a method for producing biomass from halophilic organisms, in which the halophilic organisms are fermented in a hollow space in a salt dome and said halophilic organisms or components thereof are isolated as biomass.

9 Claims, No Drawings

METHOD FOR PRODUCING BIOMASS

CROSS-REFERENCE TO RELATED APPLICATIONS

This application claims priority to International Application PCT/EP01/14600 filed Dec. 12, 2001 and to German Patent Application No. 100 62 030.2 filed Dec. 13, 2000.

The present invention concerns a method for producing biomass from halophilic organisms on an industrial scale.

The production of biomass on a commercial scale is usually carried out in fermentation plants. These consist essentially of one or more closed vessels which typically have volumes of 10 to 20 m$^3$, and in individual cases of even up to 100 m$^3$. Furthermore technical plants require auxiliary equipment for filling and emptying the culture vessels and for monitoring the culture conditions.

Fermentation in open tanks could also be considered for the production of large amounts of biomass. However, a disadvantage of such procedure is that there is a continuous risk of external contaminants entering the culture medium. In addition when the process is carried out in open tanks, fermentation broth and the organisms contained therein may be carried into the environment and released there. This is not acceptable especially when genetically modified organisms are processed which may be subject to special safety regulations or if other organisms are to be used which are classified as hazardous or toxic.

Hence an object of the invention was to provide a production process for biomass which enables the production of large volumes compared to the prior art using uncomplicated apparatus and at low cost and at the same time fulfils the requirements of the current safety regulations for microorganisms and in particular for genetically modified microorganisms.

In particular the object was to provide a suitable production process for biomass from halophilic organisms.

This object is achieved according to the invention by a method for producing biomass from halophilic organisms which is characterized in that halophilic organisms are fermented in a hollow space in a salt dome and the halophilic organisms or components thereof are isolated as biomass.

The term fermentation generally refers to processes in which desired products are formed by the aerobic or anaerobic metabolism of microorganisms, or by microbial enzymes or plant or animal cell cultures. In the method according to the invention the fermentation uses halophilic organisms.

According to the invention for example tunnels or caverns in salt domes or salt mines may be used as reaction vessels for a fermentation. The volume of such tunnels or caverns is orders of magnitudes larger than the one of artificial fermentation vessels. Considerable amounts of biomass can be produced in this manner without requiring the provision of expensive large-scale production plants. Salt caverns are usually formed in salt domes, salt mines or salt deposits by solution mining. Salt caverns remaining after solution mining the salt typically have dimensions of for example a diameter of about 20 to 200 m, in particular about 60 m and heights of about 100 to 500 m, in particular about 300 m. Such salt caverns can have volumes of several thousand cubic meters, for example of about 500,000 to 800,000 m$^3$ and thus represent enormous reaction vessels which are used according to the invention to manufacture biomass.

The favourable properties of salt (in particular rock salt, NaCl) enable almost an completely sealing from the environment. Consequently salt caverns are ideally impermeable and stable in order to serve as a reaction chamber for fermentation. Furthermore the subterranean tunnels and caverns can be completely closed off from the environment so that production can also be carried out while observing the most stringent safety regulations. A contamination of the environment or by the environment which is a major problem with open tanks and other reaction vessels is excluded by the process according to the invention.

There are a large number of abandoned caverns and tunnels in salt mines worldwide providing readily available and advantageous reaction vessels. Such salt caverns have for example been previously used as storage depots for waste materials, in particular radioactive waste and to store crude oil or natural gas. This conventional usage of salt caverns is described for example under http://www.kbbnet.de.

Another field of application from the prior art is the utilization of subterranean caverns e.g. salt caverns for the specific degradation of organic material (e.g. coal) to for example form methane with the aid of microorganisms.

U.S. Pat. Nos. 4,826,769 and 4,845,034 describe the degradation of coal by a biochemical reaction to form products such as methane by anaerobic microorganisms in subterranean hollows such as subterranean salt caverns.

U.S. Pat. No. 6,143,534 relates to the isolation of gaseous fuel gases from lignin substrates (such as coal) by a biochemical reaction which uses suitable anaerobic microorganisms. Halophilic microbes are used under anaerobic conditions to form methane in particular in a biogassification reaction using subterranean salt caverns as a reaction vessel according to U.S. Pat. No. 6,143,534.

In contrast to this prior art hollow spaces in salt domes are not used in the present invention to culture microorganisms in order to degrade or convert organic material, but rather the synthesis of biomass is described. According to the invention halophilic organisms are cultured and the halophilic organisms or components thereof are isolated as biomass.

Numerous fermentations have to be carried out under anaerobic conditions due to the organisms that are used. Since the hollow spaces that are used according to the invention such as caverns can easily be sealed airtight, anaerobic conditions can be set up in a simple manner in the culture medium. Hence in a preferred embodiment of the method according to the invention the fermentation is carried out under anaerobic conditions. A major advantage of the process according to the invention is that the oxygen content of the atmosphere in which the process is carried out can be regulated. This means that it is possible to operate under anaerobic, partially anaerobic, aerobic or even alternately anaerobic and aerobic conditions.

Halophilic organisms are generally multiplied in an oxygen-rich (aerobic) atmosphere. In contrast the formation of biomass components such as the purple membrane is induced in an oxygen-depleted or anaerobic atmosphere. In the method according to the invention the halophilic organisms are preferably multiplied under aerobic conditions and the formation of biomass components such as the purple membrane is induced under anaerobic conditions.

It is also possible to carry out the process completely in a partially anaerobic range so that growth and induction occur concurrently. If the aim is only to multiply the halophilic organisms, the entire process can be carried out aerobically. This is for example of advantage when the ultimate aim is not to obtain for example the purple membrane but other components of the biomass such as DNA and proteins.

In an anaerobic process the process is carried out oxygen-free or with small amounts of up to <3 vol %, preferably ≦2.5 vol. %, more preferably ≦2 vol. % and most preferably ≦1.5 vol % oxygen. Anaerobic means in particular completely oxygen-free (=0% oxygen content) or in the presence of a slight amount of oxygen of e.g. ≧0.5, ≧1 vol. %.

A partially anaerobic process means that the procedure is carried out with oxygen contents of 3 to 8 vol. %. The oxygen content is preferably set to 3.5 to 5 vol. %.

The oxygen content in an aerobic process is usually between >8 vol. % and the oxygen content of air, i.e. about 23 vol. %, preferably ≧10 vol. % and more preferably ≧15 vol. %, When reference is made to oxygen content, it relates to the oxygen content in the gas mixture that is fed into the reaction medium or to the oxygen content above the reaction medium. The oxygen content in the gas phase can be measured by conventional methods e.g. by means of oxygen electrodes.

The oxygen content is adjusted according to the desired process. This can be achieved in a simple manner for example by using plastic tubes having a controlled porosity.

The amount of oxygen dissolved in the reaction solution depends on the amount of oxygen supplied or on the amount of oxygen present in the gas phase, whereby an equilibrium is established between the oxygen dissolved in the salt solution and the oxygen present in the gas phase. In the process according to the invention oxygen is passed into the reaction medium or into the gas phase which then accordingly dissolves in the salt solution. Under the aerobic conditions that are then present, the organisms multiply and consume oxygen in this process to form an anaerobic medium if no further oxygen is supplied. It may be gassed again depending on whether further multiplication is desired. If it is intended to induce the formation of for example the purple membrane, the anaerobic conditions are maintained. If the gassing is carried out at an appropriate frequency, it is possible to operate under completely aerobic conditions. A complete anaerobic process is achieved when gassing does not take place. In order to keep the process continuously in a partially anaerobic range, a constant $O_2$ level can be maintained by gassing at intervals.

The solubility of oxygen in the aqueous salt solution depends on the temperature. Common fermentation temperatures are preferably 10 to 80° C., more preferably 25 to 45° C., and most preferably 30 to 40° C. In order to set the required temperatures, it may be necessary to heat the medium. This can be achieved by conventional methods or also optionally by solar radiation.

Halophilic, preferably halotolerant or/and extremely halophilic organisms and particularly preferably halobacteria are cultured in the method according to the invention to produce biomass. *Halobacterium salinarum* or/and *Haloferax volcanii* are preferably cultured. Such organisms are cultured in salt-containing media where the salt content is adjusted according to the organism to be cultured. In general the medium should have a salt content of about 5% by weight up to the content of a saturated solution e.g. up to about 40% by weight. At room temperature a saturated salt solution contains about 26% by weight salt. A salt solution containing about 5% by weight corresponds approximately to the salt concentration of sea-water.

Halophilic ("salt-loving") organisms are organisms which grow optimally in media containing about 5% by weight salt i.e. in a ca. 1 M salt solution i.e. they can for example be cultured in sea-water. Such organisms are viable at salt concentrations of at least about 3% by weight.

Extremely halophilic organisms and halotolerant organisms grow optimally at salt concentrations of >2.5 M (ca. >15% by weight salt solution). Examples of extremely halophilic organisms are *Haloferax volcanii* and *Halobacterium salinarum*. Extremely halophilic organisms are viable at concentrations of about 10>% by weight.

Although halotolerant organisms can grow in an extremely salty environment (>2.5 M), they do not have the high salt content in the cell, but rather they compensate the osmotic pressure by producing a suitable substance. Dunaniella is for example a halotolerant species which produces glycerol. These organisms are viable at low as well as at very high salt concentrations (saturated solution) e.g. at about 26% by weight salt.

The fermentation plants known in the prior art would need considerable additional expensive apparatus to ferment halophilic and in particular extremely halophilic or/and halotolerant organisms, since it is necessary to use culture vessels that are very resistant to corrosion for example culture vessels with a ceramic coating. The process according to the invention in a hollow space in a salt dome does not require this additional apparatus. Moreover, since a cavern in a salt dome is used as a reaction vessel, the very large amounts of salt required to culture halophilic organisms are directly available. For example the salt can be simply washed with water from the wall of the cavern into the fermentation broth which automatically yields the high salt concentrations necessary to culture halophilic organisms. This simple system enables a constant cell density to be maintained which results in particularly good yields. By simply adding or removing water, it is possible to adapt the volume of the fermentation solution to the desired cell density whereby the desired concentrated salt solution is automatically formed again since salt precipitates when water is removed and an adequate amount of salt is dissolved from the walls or from the store at the bottom when water is added. A saturated salt solution which has a salt content of preferably ca. 26% by weight at room temperature is preferably used to ferment halophilic organisms in a hollow space in a salt dome. An additional advantage of carrying out fermentations in saturated salt solutions is that contamination by other interfering microorganisms practically does not occur at such high salt concentrations. If a salt concentration is required to culture the organisms which is lower than that of a saturated solution, the appropriate concentrations of the solution can be adjusted by continuously adding water at a certain feed rate such that the salt dissolves more slowly from the wall or from the bottom of the vessel than the water addition. In this manner it is possible to culture organisms that grow optimally in concentrated but not saturated salt solutions whereby in this case the cell density can also be regulated and kept constant.

Furthermore there are no transport or storage costs since the salt required for the culture is directly available at the production plant.

Halobacterial strains that produce bacteriorhodopsin, purple membrane, white membrane, halorhodopsin, sensor rhodopsin I or/and II, ATPases, flagellar motors and other enzymes or products that can be used technically are a particularly interesting class of extremely halophilic organisms. According to the invention substances can also be produced as fermentation products which are obtained by modification and in particular by genetically engineering the said products as well as products which are only produced by the microorganisms after a genetic modification. Hence according to the invention it is possible to obtain all known products of halobacteria as well as these products in a modified form as a biomass. Moreover, it is also possible to produce non-natural products in microorganisms especially in halobacteria i.e. products which the microorganisms produce after the corresponding genetic information has been incorporated into them. In this case the microorganisms and in particular the halobacteria act as a pure host.

However, in order to obtain the desired products such as bacteriorhodopsin, it is often necessary when culturing halobacterial strains to additionally illuminate the culture medium with light or to carry out an anaerobic culture. Since, as already elucidated above, an anaerobic process is easily possible with the method according to the invention, it is possible to omit the components required by the prior art which enable an illumination or gassing or evacuation.

Furthermore, since the required amounts of salt for the fermentation of halophilic organisms can be taken directly from the salt deposit or the salt dome, the method according to the invention is considerably more economical than conventional methods with regard to technical apparatus, logistics and costs.

The method according to the invention can also be used to culture genetically modified organisms. In this manner it is possible to obtain specific, desired, optionally modified fermentation products. The processing of genetically modified organisms is possible since the caverns can easily be completely closed off from the outside world and thus it is possible to almost completely prevent contamination into and out of the culture medium in addition to excluding air.

Hence the method according to the invention allows obtaining large amounts of the desired component of halophilic organisms such as bacteriorhodopsin or a genetically modified bacteriorhodopsin, the purple membrane, the white membrane or another product produced in cell cultures as a fermentation product. For example biomass can be obtained per cavern in an amount of about 50 tons per year. The biomass can be removed continuously or batch-wise from the medium.

When an appropriate procedure is used, the cultured halophilic organisms contain other components such as DNA and soluble proteins which can also be recovered as a biomass. DNA or/and soluble proteins can for example be partially or completely lysed directly on the site (acidically or alkaline or mechanically or thermal) and then be used as carbon sources for other fermentations or also be isolated as biomass.

The hollow spaces that are used can be natural or artificially formed hollow spaces in a salt dome or salt deposit. Artificial hollow spaces are formed in particular when salt formations are solution mined to obtain salt. The hollow spaces can have any volumes and volumes of the order of magnitude of several hundred thousand $m^3$ are common for salt caverns.

The use according to the invention of hollow spaces in salt domes as reaction vessels for the production of biomass or for the production of desired fermentation products in large amounts has the following special advantages. Firstly the costs per fermentation volume are substantially less than with conventional fermentation plants since salt caverns already exist in large numbers and are usually unused. Furthermore the enormous amounts of salt that are required to ferment extremely halophilic organisms can be taken economically directly from the salt dome so that there are also no transport or storage problems. Furthermore, caverns in salt domes can easily be completely closed off from the outside world. This prevents contamination of the fermentation broth from impurities from outside and also prevents components of the fermentation broth such as organisms and in particular genetically modified organisms from entering the environment. Consequently it is possible to set up a production using genetically modified organisms even under the strictest biological safety regulations. The isolation from the outside world also enables the reaction to be carried out under anaerobic conditions.

Since salt caverns are completely surrounded by thick layers of salt, there is no connection whatsoever with the ground water. Hence this rules out contamination of the ground water by components or microorganisms from the fermentation medium. This is also an advantage of hollow spaces in salt domes compared to normal caves since caves usually have fissures etc. of one kind or another.

Another technical advantage of the method according to the invention is that the fermentation medium can be used directly as liquid salt for example to de-ice roads after the fermentation and separation of the microorganisms. Since halobacteria for example lyse when water is added, they would automatically lyse when they are discharged into the environment with the resulting dilution with water such that a subsequent use of the salt solution is safe.

The fermentation itself is preferably carried out in a subterranean artificial salt lake which is formed by spraying, injecting or flushing water into the hollow space. The artificial salt lake is preferably formed by flushing salt from the walls of the cavern with water in order to directly form the desired nutrient medium. The required salt concentrations can be adjusted in this process. In this manner the salt required to culture halophilic bacteria can be simply added without requiring technically complicated apparatus.

EXAMPLE

The method according to the invention is preferably carried out as follows:

Production of the Fermentation Broth

A salt solution is firstly formed by flushing salt from the walls of the cavern with water. Subsequently the ionic composition of the salt solution can be analysed and the solution can be supplemented if necessary by adding other ions, e.g. potassium, magnesium, calcium, in amounts that are required for the fermentation. The salt lake that is formed can if necessary be thermostatted by stirring or pump circulating the salt brine depending on the size of the cavern. Salt brine is preferably drawn with a pipe from the bottom of the lake to the top, thermostatted and then returned to the top of the lake. Thermostatting can further increase the growth of the microorganisms and hence the amount of fermentation product. Finally carbon sources can be added to the salt solution for the fermentation, for example peptone or starch hydrolysates.

Fermentation Procedure

The salt lake produced as described above which serves as the fermentation broth is inoculated with a bacterial culture and in particular a halobacterial culture. Subsequently the growth of the bacteria is monitored until an acceptable or predetermined cell density is reached. Afterwards the biomass that is formed is separated from the medium. The separation can be carried out continuously e.g. by so-called cross-flow filtration (cross-flow module). It is also possible to remove the biomass in a batch process. The amount of salt that is removed together with the biomass is resupplied by the temperature-dependent saturation solubility of salt in water or the salt brine is continuously removed from the walls by simply dissolving.

The invention claimed is:

1. A method for producing biomass from extreme halophilic organisms, comprising fermenting extreme halophilic organisms for biosynthesis of biomass on the surface of a hollow space in a salt dome within a subterranean salt cavern at a level below earth having a temperature such that no additional heat is required for fermentation, wherein the fermentation is carried out at least partially anaerobically and wherein the extreme halophilic organisms grow optimally at a saturated salt concentration of at least about 2.5 M, and isolating bacteriorhodopsin, purple membrane or white membrane from the fermented extreme halophilic organisms.

2. The method of claim 1, wherein the method is firstly carried out aerobically to multiply the extreme halophilic organisms and then anaerobically to induce the formation of biomass components.

3. The method of claim 1, wherein *Haloferax volcanii* or *Halobacterium salinarum* are used.

4. The method of claim 1, wherein a natural hollow space or one that is formed artificially is used.

5. The method of claim 1, wherein the amounts of salt required for the fermentation of extreme halophilic organisms are taken from the salt dome.

6. The method of claim 1, wherein genetically modified organisms are used.

7. The method of claim 1, wherein the saturated salt concentration is at least about 15% by weight.

8. The method of claim 1, wherein the saturated salt concentration is at least about 26% by weight.

9. The method of claim 1, wherein the saturated salt concentration is at least about 40% by weight.

* * * * *